United States Patent [19]

Matsuo

[11] 4,269,192
[45] May 26, 1981

[54] STABBING APPARATUS FOR DIAGNOSIS OF LIVING BODY

[75] Inventor: Kazumasa Matsuo, Hachioji, Japan

[73] Assignee: Olympus Optical Co., Ltd., Tokyo, Japan

[21] Appl. No.: 44,570

[22] Filed: Jun. 1, 1979

[30] Foreign Application Priority Data

Dec. 2, 1977 [JP] Japan .................. 52-162019

[51] Int. Cl.³ ............................ A61B 1/00; A61B 5/00
[52] U.S. Cl. ................................ 128/665; 128/329 R; 128/347; 128/6
[58] Field of Search .................... 128/634, 6, 665–667, 128/753, 754, 329, 347

[56] References Cited

U.S. PATENT DOCUMENTS

| | | |
|---|---|---|
| 3,556,085 | 1/1971 | Takahashi .................. 128/6 |
| 3,889,656 | 6/1975 | Krawitt . |
| 3,961,621 | 6/1976 | Northeved .................... 128/753 |
| 4,058,114 | 11/1977 | Soldner ...................... 128/754 |
| 4,175,545 | 11/1979 | Termanini ................... 128/6 |
| 4,181,123 | 1/1980 | Crosby ...................... 128/6 |

FOREIGN PATENT DOCUMENTS

| | | |
|---|---|---|
| 836392 | 4/1952 | Fed. Rep. of Germany . |
| 2292457 | 6/1976 | France . |
| 2317903 | 2/1977 | France . |
| 46-4105 | 6/1971 | Japan ...................... 128/665 |

OTHER PUBLICATIONS

Edholm P. et al., Med. & Biol. Engng, vol. 6, No. 4, Aug., 1968, pp. 409–413.

Primary Examiner—Kyle L. Howell

[57] ABSTRACT

A stabbing apparatus for diagnosis of living body comprising a tubular member (1) having a sharp-edged tip end portion (X), a first light guide means (5) inserted in the tubular member (1) and having one end disposed at the tip end portion (X), a second light guide means (6) inserted in the tubular member (1) and having one end disposed at the tip end portion (X), a light source means (8) applying light to the other end of the first light guide means (5) in order to deliver light through the tip end portion (X), and a photosensing means (10) at the other end of the second light guide means (6) for sensing light reflectedly applied to the tip end portion (X). The photosensing means (10) of the apparatus discriminatingly indicates situations where the tip end portion (X) is within the abdominal wall of a living body and where the portion (X) has passed through the abdominal wall.

4 Claims, 7 Drawing Figures

STABBING APPARATUS FOR DIAGNOSIS OF LIVING BODY

BACKGROUND OF THE INVENTION

This invention relates to a stabbing apparatus which may be used as a pneumoperitoneum neddle, trocar or injector needle.

In observing or operating on the body cavity by means of a laparoscope, for example, a pneumoperitoneum needle is first stabbed into the abdominal wall of a living body to inject the body cavity with gas, the abdominal wall is bored by means of a trocar, and then the laparoscope is inserted into the body cavity through a resultant bore.

When using the pneumoperitoneum needle or trocar, the tip end of the needle stabbed into the abdominal wall must be sure to reach the body cavity, whereas it should be avoided to damage any internal organs by too deep stabbing of the needle.

Heretofore, however, the stabbing operation has depended on the skill of an operator, without positively detecting the depth of stabbing of the needle such as pneumoperitoneum needle or trocar, that is, without checking to see if the needle has pierced the abdominal wall or if the needle may not damage any internal organ. Thus, the operation has not been enjoying very good reliability and safety; gas injection might be started with a bore in the abdominal wall not reaching the body cavity or some internal organ might be stabbed with the needle.

SUMMARY OF THE INVENTION

The object of this invention is to provide a stabbing apparatus with improved reliability and safety, capable of checking to see if the tip end portion of a needle stabbed into a body wall is staying therein or if it has passed through the body wall to reach an internal organ.

In order to attain the above object, the stabbing apparatus according to this invention comprises a tubular member having a sharp-edged tip end portion, a first light guide means inserted in the tubular member and having one end disposed at the tip end portion, a second light guide means inserted in the tubular member and having one end disposed at the tip end portion, a light source means applying light to the other end of the first light guide means in order to deliver light through the tip end portion, and a photosensing means at the other end of the second light guide means for sensing light reflectedly applied to the tip end portion.

The apparatus of the above-mentioned construction can discriminatingly indicate situations where the tip end portion is within, for example, the abdominal wall of a living body and where it has passed through the abdominal wall. That is, while the tip end portion is staying in the abdominal wall, light emitted from one end of the first light guide means is reflected by the abdominal wall tissue, and returned to the photosensing means via the second light guide means. When the tip end portion has passed through the abdominal wall, on the other hand, the light from one end of the first light guide means ceases to be reflected by the abdominal wall tissue. Then, hardly any light is returned to the photosensing means. The photosensing means perceives the existence of light emitted from the other end of the second light guide means or change in quantity of light, and indicates the state or position of the tip end portion relative to the abdominal wall. When the tip end portion, after piercing the abdominal wall, is further thrusted into the living body to approach the surface of an internal organ, the light from the first living guide means is reflected on the surface of the organ, and again returned to the photosensing means. The photosensing means detects the light, and gives an alarm that the tip end position has approached the internal organ. Further, a needle equipped detachable tubular member of variable size is preferably used for such checking.

DETAILED DESCRIPTION OF THE PREFERRED EMBODIMENTS

Figure 1:
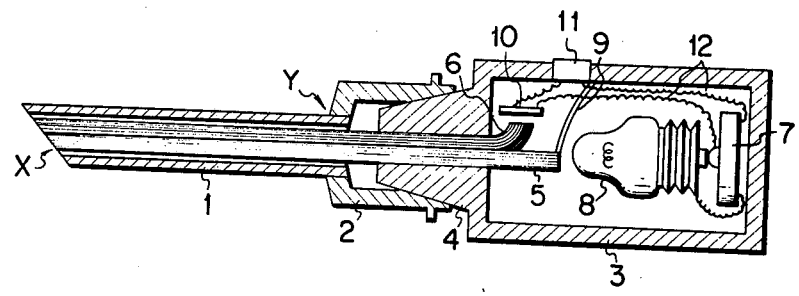
FIG. 1 is a profile showing an outline of the stabbing apparatus according to this invention.

Now there will be described preferred embodiments of this invention with reference to the accompanying drawings in which like reference numerals refer to the same or similar parts throughout the several views, to avoid repeated description.

Referring now to the drawing of FIG. 1, numeral 1 designates an outer tube whose tip end X is beveled to be sharp-edged and rear end is fitted with a cylindrical coupler 2 with the inner peripheral surface of its open end tapered. The coupler 2 is removably fitted with a case 3. On one end face of the case 3 is a projection 4 with a tapered outer peripheral surface matching with the tapered surface of the coupler 2. The case 3 may be removably attached to the outer tube 1 by fitting the projection 4 into the coupler 2. A first light guide fiber 5 for light admission and a second light guide fiber 6 for light sensing are taken out from the projection 4 of the case 3, and inserted in the outer tube 1. The tip ends of these fibers 5 and 6 are so cut as to be flush with the slanting surface at the tip end X of the outer tube 1.

Inside the case 3, there are provided a battery 7 as a power source and a lamp 8 electrically connected to the battery 7. Also inside the case 3 is a shade 9 for preventing light from the lamp 8 from being directly admitted into a photosensitive device 10 mentioned later. The light from the lamp 8 is to be admitted into the light guide fiber 5 through the rear end face thereof. Moreover, the case 3 contains therein the photosensitive device 10 such as a photo transistor facing the rear end face of the light guide fiber 6 and an indicator device 11 such as an LED exposed on one side of the case 3. The LED 11 and the photo transistor 10 constitute a photosensing means 10. The means 10 and the battery 7 are electrically connected with each other by means of lead wires 12.

Figure 2A:
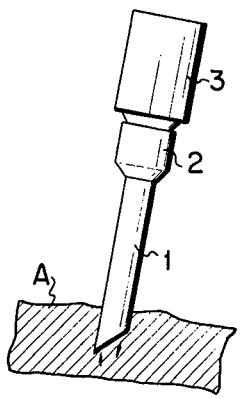
FIGS. 2A to 2C shown varied operating situations for the apparatus of FIG. 1.
Figure 2B:
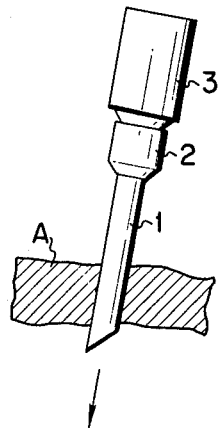
Figure 2C:
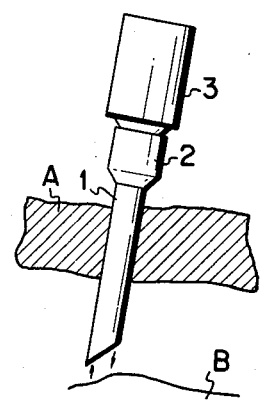

Referring now to FIGS. 2A to 2C, there will be described the function of the apparatus of the aforementioned construction. First, the tip end X of the outer tube 1 is stabbed into e.g. an abdominal wall A of a living body. When the tip end X is within the abdominal wall A as shown in FIG. 2A, the light admitted into the light guide fiber 5 from the lamp 8 is emitted from the forward end face of the fiber 5. The emitted light is reflected by the tissue of the abdominal wall A and admitted into the light guide fiber 6 through the forward end face thereof, thus turning on the LED 11 by means of the photo transistor 10. When the tip end X of the outer tube 1 has passed through the abdominal wall A, as shown in FIG. 2B, the light radiates into the body cavity through the forward end face of the light guide fiber 5. In consequence, no light will be admitted into the light guide fiber 6, so that the LED 11 will not be turned on. Further, when the outer tube 1 is inserted deep into the body cavity to ring its tip end X close to an internal organ B, as shown in FIG. 2C, the light from the light guide fiber 5 is reflected on the surface of the organ B and admitted into the light guide fiber 6, thus again turning on the LED 11. Accordingly, the position of the tip end X of the outer tube 1 inside the living body may be detected by checking to see if the LED 11 is on.

Figure 3:
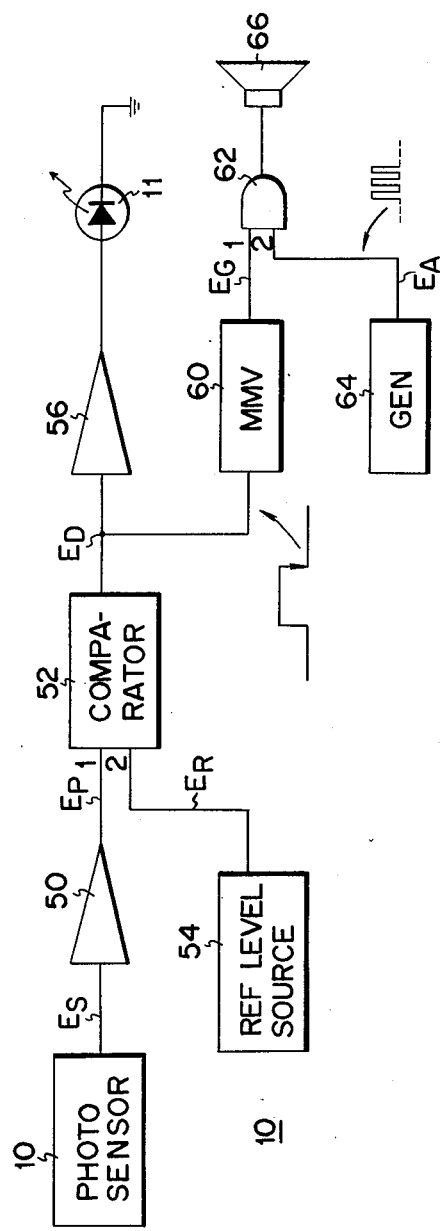
FIG. 3 shows a modified example of a photosensing means applicable to the apparatus of FIG. 1.

FIG. 3 shows a modified arrangement of the photosensing means 10 as shown in FIG. 1. The photosensitive device or photo transistor 10 produces an electric signal $E_S$ corresponding to a given intensity of light. The signal $E_S$ is amplified by an amplifier 50 into a signal $E_P$ at a suitable level, which is applied to a first input terminal of a comparator 52. A second input terminal of the comparator 52 is supplied with a reference signal $E_R$ from a reference level source 54. The comparator 52 compares the levels of the signals $E_P$ and $E_R$ to deliver a detection signal $E_D$ if $E_P > E_R$, for example. The signal $E_D$ is supplied to the LED 11 through an amplifier 56. Namely, when the photo transistor 10 perceives an intensity of light above a predetermined level, the signal $E_D$ is produced to turn on the LED 11.

The signal $E_D$ is applied also to a monostable multivibrator (MMV) 60. The MMV 60 is triggered by a fall or disappearance of the signal $E_D$. Then, the MMV 60 supplies a gate signal $E_G$ at logic level "1" to a first input terminal of an AND gate 62 for a fixed time. This fixed time is determined in accordance with the time constant of the MMV 60 itself. A second input terminal of the AND gate 62 is supplied with an alarm signal $E_A$ of e.g. 1 kHz from an alarm generator 64. When the MMV 60 is triggered to turn the logic level of the gate signal $E_G$ to "1", the AND gate 62 is opened. Then, the alarm signal $E_A$ is supplied to a loudspeaker 66 via the AND gate 62. That is, when the intensity of light applied to the photo transistor 10 is lowered below the aforesaid predetermined level after the photo transistor 10 has sensed the intensity above such level, the MMV 60 is triggered. Thus, the loudspeaker 66 produces an alarm sound to give notice that the tip end X has pierced the abdominal wall of the living body.

Figure 5:
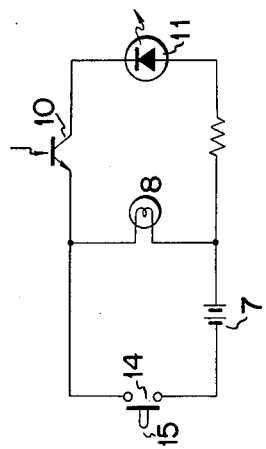
FIG. 5 is a circuit diagram illustrating an electric circuit of the apparatus of FIG. 4.
Figure 4:
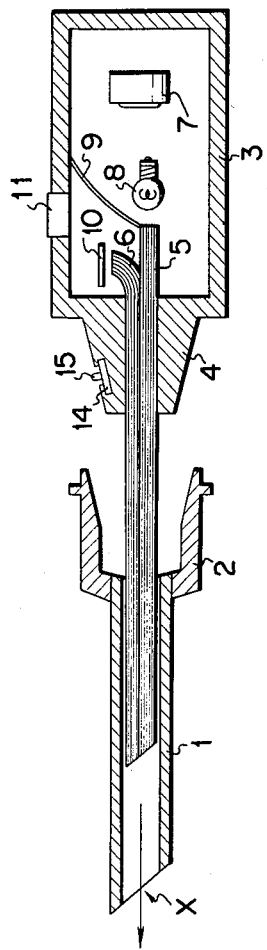
FIG. 4 is a profile of a modified arrangement in which the apparatus as shown in FIG. 1 is provided with a power switch.

It is to be understood that the invention is not limited to the above-mentioned embodiment, and that the LED 11 may be replaced by a neon tube, liquid crystal device or buzzer, for example. Also, there may be provided a switch 14 as shown in FIG. 4 which allows an electric circuit as shown in FIG. 5 to operate only when the case 3 is attached to the outer tube 1, for the prevention of unnecessary dissipatin of the battery. The switch 14 is turned on when a projection 15 is depressed by the tapered inside surface of the coupler 2. Moreover, the stabbing apparatus of this embodiment may be used as an injector needle as well as the pneumoperitoneum needle and trocar.

In the apparatus according to this invention, as described above, the case from which the light guide fibers for light admission and sensing are taken out, containing the light source sending out light to the light guide fiber for light admission and the photosensing means to detect light fom the light guide fiber for light sensing, may be removable attached to the rear end of the outer tube with the sharpened tip end by inserting the pair of light guide fibers into the outer tube. Thus, the position of the tip end X of the outer tube inside the living body may be detected by the photosensing means. Accordingly, the stabbing operation can be performed properly without depending on the skill or intuition of operators that has conventionally been essential to the operation, so that there may be obtained a good practical effect that the stabbing operation can be achieved securely and safely without involving insufficient stabbing depth or wrong stabbing of internal organs.

Although specific constructions have been illustrated and described herein, it is not intended that the invention be limited to the elements, devices and/or circuit constructions disclosed. One skilled in the art will recognize that the particular elements, devices or subcircuits may be used or combined without departing from the scope and spirit of the invention.

What is claimed is:

1. In a stabbing apparatus for diagnosis of a living body having;
    a tubular member having a sharp-edged tip end portion;
    a first light guide means inserted in said tubular member and having one end disposed at said tip end portion;
    a second light guide means inserted in said tubular member and having one end disposed at said tip end portion;
    a light source means applying light to the other end of said first light guide means in order to deliver light through said tip end portion; and
    a photosensing means at the other end of said second light guide means for sensing light reflected to said tip end portion; the improvement wherein at least the tip end portions of said first and second light guide means are made of substantially rigid material;
    said tubular member has a cylindrical coupler with the inner peripheral surface of the opening thereof tapered and disposed at the opposite end portion to said tip end portion, a case containing said light source means and said photosensing means at the other end side of said first and second light guide means, and a projection on said case having along the outer periphery thereof a tapered surface matching with the tapered surface of said coupler, and penetrated by said first and second light means, whereby said tubular member and said case are coupled with each other by means of the tapered surfaces of said coupler and said projecton engaging each other;
    said photosensing means including a photosensitive device disposed at the other end face of said second light guide means, whereby a signal corresponding to the intensity of light emitted from said other end face is delivered, and an indicator device mounted at a given position of said case to indicate the existence of tissue and to reflect light just in front of said tip end portion in accordance with the signal from said photosensitive device.

2. A stabbing apparatus according to claim 1 wherein said case further contains a power source supplying power to said light source means and said photosensing means, and said projection is provided on the tapered surface thereof with a switch means for switching the power supply, said switch means being turned on when said projection is fitted in said coupler.

3. A stabbing apparatus according to claims 1 or 2, wherein said photosensing means includes a photosensitive device disposed at the other end face of said second light guide means whereby a first signal ($E_S$) corresponding to an intensity of light emitted from said other end face is delivered, a reference level source producing a reference signal ($E_R$), a comparator comparing said reference signal ($E_R$) with a second signal ($E_P$) proportional to said first signal ($E_S$) and producing a third signal ($E_D$) when the level of said second signal ($E_P$) is above or below that of said reference signal ($E_R$), and an indicator device indicating the existence of tissue to reflect light just in front of said tip end portion in accordance with said third signal ($E_D$).

4. A stabbing apparatus according to claim 3, wherein said photosensing means further includes a monostable multivibrator triggered by disappearance of said third signal ($E_D$) to produce a fourth signal ($E_G$) for a fixed time, an alarm generator producing a fifth signal ($E_A$) for producing an alarm, a gate circuit producing the logical product of said fourth and fifth signals ($E_G$, $E_A$), and an alarm device to perform said alarm when the logic levels of said fourth and fifth signals ($E_G$, $E_A$) both become "1" in said gate circuit.

* * * * *